United States Patent [19]

Siebert et al.

[11] Patent Number: 4,479,867
[45] Date of Patent: Oct. 30, 1984

[54] ELECTROCHEMICAL SYSTEM FOR MEASURING THE PARTIAL OXYGEN PRESSURE IN A GASEOUS OR LIQUID ATMOSPHERE

[75] Inventors: Elisabeth Siebert; Jacques Fouletier, both of Grenoble; Serge Vilminot, Castries, all of France

[73] Assignee: Societe Nationale Elf Aquitaine, Courbevoire, France

[21] Appl. No.: 518,919

[22] Filed: Aug. 1, 1983

[30] Foreign Application Priority Data

Aug. 2, 1982 [FR] France ............................. 82 13473

[51] Int. Cl.³ ........................................... G01N 27/58
[52] U.S. Cl. .................................... 204/426; 204/421; 204/422; 204/424
[58] Field of Search ............... 204/421, 422, 424, 426, 204/15

[56] References Cited

U.S. PATENT DOCUMENTS 3,764,269 10/1973 Oldham et al. ................. 204/421 X

FOREIGN PATENT DOCUMENTS 2836900 10/1979 Fed. Rep. of Germany ...... 204/422
2916407 11/1979 Fed. Rep. of Germany ...... 204/422
WO82/00892 3/1982 PCT Int'l Appl. ................. 204/422

OTHER PUBLICATIONS

Rapp et al., "Techniques of Metals Research", Physicochemical Measurements in Metal Research, part 2, vol. 4, 1970, pp. 132–135.

Kleitz et al., "New Types of Solid-Electrolyte Gas Sensors", Electrodes and Electrolytes, Lake Geneva, WI, USA, May 1979, pp. 69–73.

Primary Examiner—G. L. Kaplan
Assistant Examiner—Nam X. Nguyen
Attorney, Agent, or Firm—Weiser & Stapler

[57] ABSTRACT

Electrochemical system for measuring the partial pressure of oxygen in a gaseous or liquid atmosphere, in which the electrolyte is a halogenide mixture doped with peroxide ions. This system constitutes an oxygen gauge permitting measurements at temperatures below 200° C.

19 Claims, 2 Drawing Figures

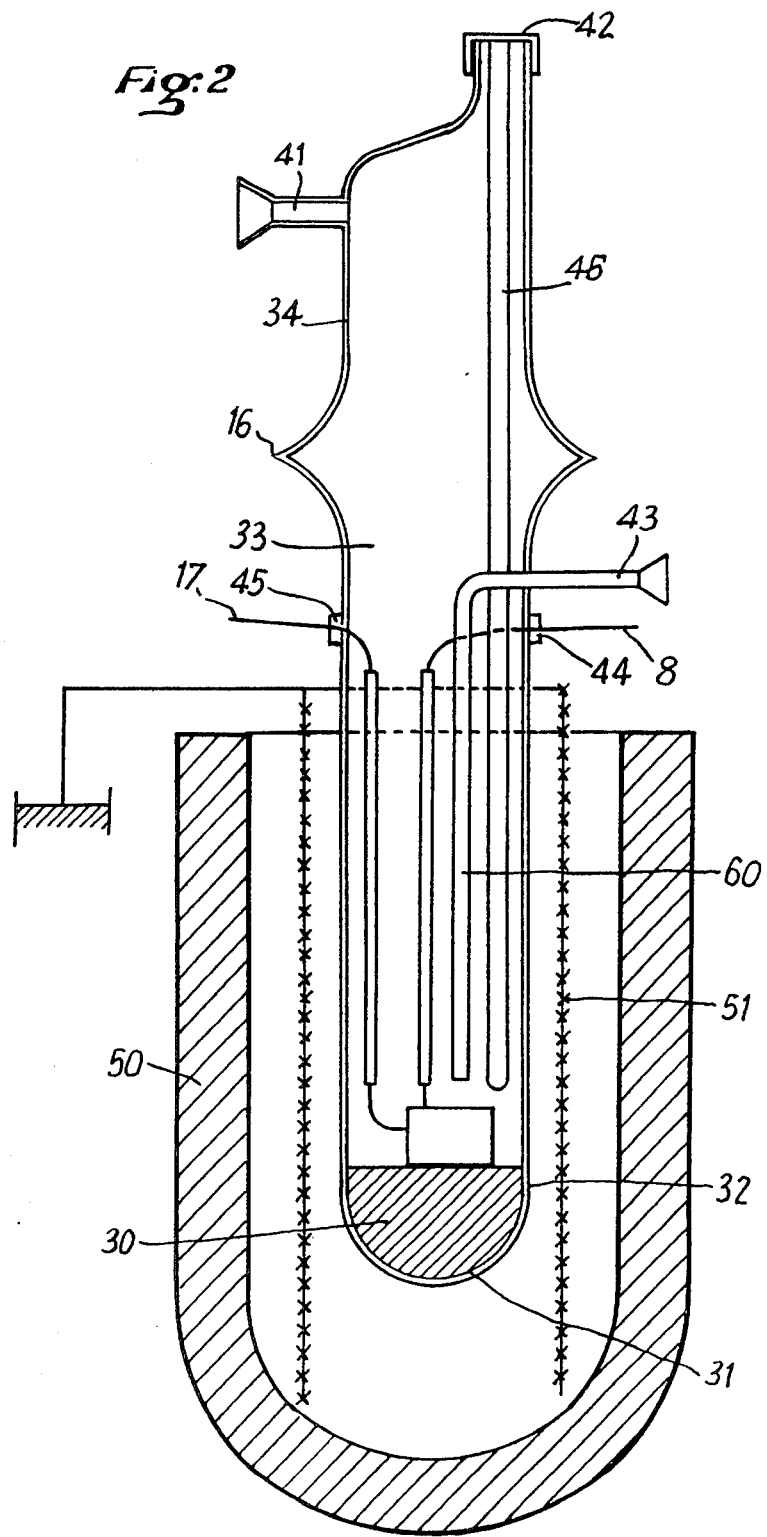

ELECTROCHEMICAL SYSTEM FOR MEASURING THE PARTIAL OXYGEN PRESSURE IN A GASEOUS OR LIQUID ATMOSPHERE

The present invention relates to an electrochemical system for measuring the partial pressure of oxygen in a gaseous or liquid atmosphere, which can also be called an electrochemical oxygen gauge.

It is known to obtain such oxygen gauges by associating a reference electrode and a working electrode with a solid electrolyte layer.

In the prior art systems, the solid electrolyte may be an oxide. In such an electrolyte, the $O^=$ ions provide the ionic conduction and are brought into operation by the reactions of the electrode. Such a gauge is described, for example, in French patent application No. 2,243,625, which utilizer, as the electrolyte, a solid solution of zirconium and yttrium oxide, a solid solution based on thorium. However, the use of these gauges is confined to relatively high temperatures, e.g., above 40° C., by the fact that these oxides are very poor conductors at low temperature.

It has also been proposed to overcome these drawbacks by providing electrolytes in which the ionic conductivity is furnished by ions other than oxygen, e.g., by halogenides. It is in this way that Pelloux et al, in "Solid State Ionics" Vol. 1, 1980, p. 343, have proposed an electrolyte consisting of $SrCl_2$ doped with KCl and containing a small quantity of SrO. In French patent application No. 2,486,244, entitled (in English translation) "Potentiometric System Usable as Sensor for Determining the Pressure of a Gas" it is proposed to use a fluoride mixture of the type $PbSnF_4$, in which the fluoride ions provide the conductivity.

While these electrolytes enable the construction of usable oxygen gauges, they nevertheless have the drawback of exhibiting a relatively long response time, the response time of the gauge being defined as the time necessary for the e.m.f. of the gauge to become substantially equal to the theoretical e.m.f., after a change in the oxygen pressure. Such a drawback is detrimental to those applications in which it is desired to rapidly detect a change in the content of oxygen.

Accordingly, it is an object of the present invention to provide a system which makes it possible to overcome the drawbacks of the prior art and which, in particular, exhibits a relatively short response time while being usable at low temperatures, particularly below 200° C.

This and other objects which will appear are achieved in accordance with this invention by an electrochemical system for measuring the partial pressure of oxygen in a gaseous or liquid atmosphere which comprises a working electrode responsive to the oxygen, a solid electrolyte consisting at least in part of a halogenide mixture capable of providing the ionic conduction by means of the halogen ions, a reference electrode consisting of a gas, or a solid, or a mixture of solids, said reference electrode being capable, at least in its immediate vicinity, of maintaining constant the chemical potential of the halogen in the electrolyte, this system being characterized in that the electrolyte is doped with a peroxide which provides the reactive component of the working electrode.

The advantages of the doping resides in the fact that, for such an oxygen gauge, it is the peroxide ions which are used in the electrode reaction. This permits improving its reversibility and reducing the response time of the gauge.

In addition, such an electrolyte exhibits good conductivity at ordinary temperatures and no electronic conductivity.

In accordance with a further characteristic of the invention, the electrolyte is selected from mixed halogenides which are good conductors and which provide sites capable of accepting the peroxide ions without decomposition.

Preferably, the halogenide is a fluoride mixed with lead and tin having the formula $PbSnF_4$.

According to a further characteristic, the electrolyte consists of $PbSnF_4$ in which the peroxide is present in the proportion of 0.2 to 3% (atomic percentage relative to the fluoride), and preferably 0.5 to 2%.

The reference electrode may be constituted, at least partly, by the mixture of a metal and its halogenide corresponding to the halogen of the electrolyte, the metal being selected from tin, lead, bismuth and silver.

As the measuring electrode, one can utilize a porous electrode consisting of an inert metal such as, for example, platinum and silver. This electrode may then be obtained by depositing a metallic coating layer on the electrolyte.

In another embodiment, the measuring electrode consists of an electronically conductive oxide. It is preferably obtained by oxidation, in a corresponding oxygen atmosphere. One can also produce a tablet, by means of a powder of said oxide, pressed into contact with the electrolyte. Preferably the electronically conductive oxide is the dioxide of ruthenium.

The invention will be better understood from the description of a preferred embodiment, which follows, given with reference to the accompanying drawing. This description provides an illustration of the invention, but is not under any circumstances to be considered as a limitation.

In these drawings:

FIG. 2 shows, in cross-section, a system in which the gauge shown in FIG. 1 can be operated.

Figure 1:
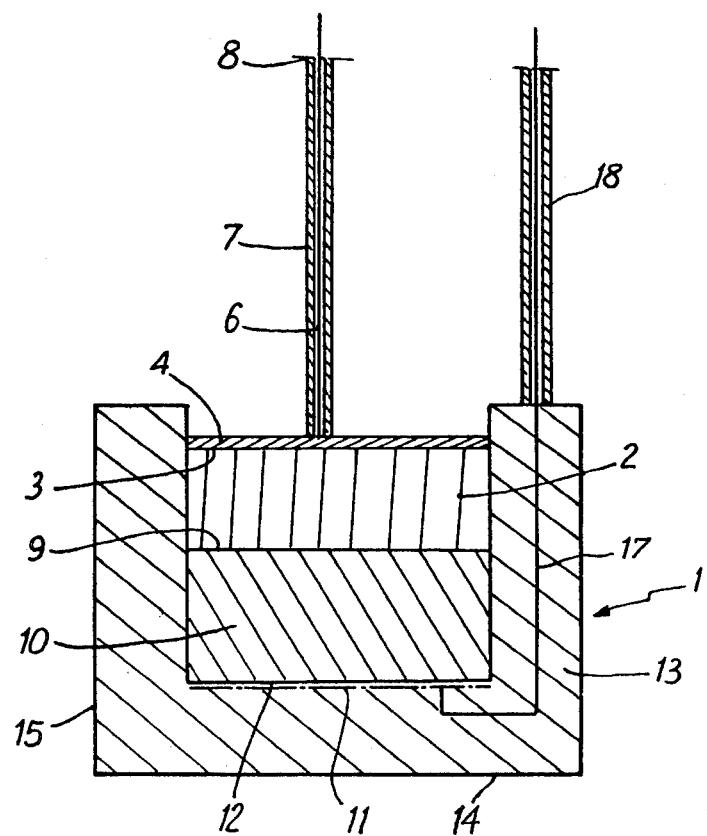
FIG. 1 shows, in cross-section, an oxygen gauge embodying the invention.

In FIG. 1, there is illustrated an oxygen gauge 1 comprising a tablet 2 of solid electrolyte. This solid electrolyte consists of a fluoride mixed with lead and tin doped with barium peroxide, in proportion of 0.5% of peroxide relative to the fluorine (atomic percentage). This doping was obtained by dissolving the barium peroxide in a mixture of powders of tin fluoride and lead fluoride.

To carry out this dissolution the mixture of powders is melted in a sealed tube in a vacuum of $10^{-4}$ millibar and this is maintained at a temperature of 250° C. for two hours.

The percentage of 0.5% of peroxide was so chosen that the peroxide ions are stable, given that the barium ions become attached to lead sites during doping.

The electrolyte tablet 2 is in contact at its lower surface 9 with the reference electrode 10 consisting of a compressed mixture of tin and tin fluoride powders. A current collector grid 11 of platinum is disposed below that face 12 of electrode 10 which is opposite to the contact face with the face 9 of the electrolyte.

On its upper face 3 the electrolyte is in contact with the measuring electrode 4 which consists of a porous disc of ruthenium dioxide to which is connected a conductive lead 6 surrounded by a protective sleeve 7 and whose extremity 8 is connected to an electronic millivoltmeter having high input impedance. The measuring electrode was obtained by producing a tablet of RuO$_2$ powder compressed simultaneously with the electrolyte and the reference electrode mixture so as to form a unitary tablet. Thus there is obtained an assembly which permits very good exchange reactions between, on the one hand, the electrolyte and the reference electrode and, on the other hand, the electrolyte and the measuring electrode.

The assembly is placed in a cup 13 comprising a bottom 14 and a cylindrical wall 15. This cup is made of a fluid-tight resin and is open toward the top.

The assembly constituted by cup 13 and electrolyte 2 is completely sealed so that the reference electrode has no contact with the ambient in which the working electrode is located.

The current collector grid 11 is connected, by a conductive lead 17 of platinum surrounded by a sleeve 18, to the same millivoltmeter as the conductive lead 6.

FIG. 2 shows a system particularly suitable for studying the operation of the oxygen gauge shown in FIG. 1.

The gauge 1 is placed on a support 30 whose surface 31 is spherical. The support 30 is of alumina. The assembly is placed in the lower, spherical portion 32 of a housing 33 made of Pyrex glass. The housing 33 comprises an upper portion 34. The upper portion 34 and the lower portion 32 are connected together by a sealed cylindrical rim 16. The upper portion 34 comprises an outlet tube 41 and a orifice 42 both of which provide sealed passages. The lower portion 32 similarly comprises an inlet tube 43 and tube pass-through 44 and 45 permitting the exit of conductor leads 8 and 17. The tube 43 is extended into the interior of the housing by an alumina tube 60 whose lower extremity opens above the measuring electrode.

A temperature gauge 46 is placed inside the housing and its upper extremity extends in sealed manner through the upper portion through orifice 42. The temperature gauge consists of a platinum sensor. A heater 50 surrounds the lower portion 32 of housing 33 and a metal shielding armature 51 is placed between the housing and the heater.

The above described system has been used to test the oxygen gauge shown in FIG. 1. This gauge may be represented by the following electrochemical chain: Pt, Sn-SnF$_2$/PbSnF$_4$-BaO$_2$(0.5%)/RuO$_2$ (powder), O$_2$ (PO$_2$). The variation of the e.m.f. of the gauge was measured as a function of the logarithm of the partial oxygen pressure inside the housing. It was observed that the linear variation of the e.m.f. as a function of P(O$_2$) conformed to the theory of Nernst's law, and also that the slope of the straight line correspond to a degree of oxidation of the oxygen equal to ($-1$). This provides good confirmation that, by doping the electrolyte with the peroxide, the reactive component of the electrode has been provided. This measurement was performed at 160° C.

In addition it was determined, for that temperature, that the gauge embodying the invention provided improved response time relative to undoped gauges, because it was found that, after a partial pressure variation of $10^{-2}$ atmospheres at 0.2 atmosphere, the response time was 6 min., whereas it exceeded 10 hours when the electrolyte is not doped.

The invention is not limited to the embodiments described but rather encompasses all variants thereof.

We claim:

1. An improved electrochemical device for measuring the partial pressure of oxygen in a liquid or gaseous atmosphere which electrochemical device has improved reversibility and shorter response time while being operative at low temperature, which electrochemical device comprises a working electrode responsive to oxygen, a solid electrolyte which comprises at least partially a halogenide mixture for providing ionic conduction by means of the halogenide ions and a peroxide for supplying the reactive ions for the working electrode and a reference electrode for maintaining constant, at least in its immediate vicinity, the chemical potential of the halogen of the electrolyte, which electrode comprises at least partially a mixture of a metal and the halogenide corresponding to that of the electrolyte.

2. The improved electrochemical device of claim 1 wherein the electrolyte is of mixed halogenides which do not cause perioxide ion decomposition.

3. The improved electrochemical device of claim 1 wherein the halogenide of the electrolyte is a fluoride mixture with lead and tin.

4. The improved electrochemical device of claim 1 wherein the peroxide of the electrolyte is barium peroxide.

5. The improved electrochemical device of claim 1 wherein the peroxide concentration in the electrolyte is in the range of 0.2 to 3 percent, measured as atomic percent relative to the fluoride.

6. The improved electrochemical device of claim 5 wherein the perooxide concentration is in the range of 0.5 to 2 percent.

7. The improved electrochemical device of claim 1 wherein the metal of the reference electrode is selected from the group consisting of tin, lead, bismuth or silver.

8. The improved electrochemical device of claim 1 wherein the working electrode is constituted of an electronically conductive oxide.

9. The improved electrochemical device of claim 8 wherein the oxide of the working electrode is ruthenium dioxide.

10. The improved electrochemical device of claim 1 wherein the working electrode, the electrolyte and the reference electrode are tablets pressed together, forming a unitary tablet.

11. The improved electrochemical device of claim 10 wherein the electrolyte contains a peroxide which is barium peroxide.

12. The improved electrochemical device of claim 11 wherein the peroxide concentration in the electrolyte is in the range of 0.2 to percent, measured as atomic percent relative to the fluoride.

13. The improved electrochemical device of claim 12 wherein the peroxide concentration is in the range of 0.5 to 2 percent.

14. The improved electrochemical device of claim 10 wherein the electrolyte is of mixed halogenide which do not cause perioxide ion decomposition.

15. The improved electrochemical device of claim 14 wherein the halogenide of the electrolyte is a fluoride mixture with lead and tin.

16. The improved electrochemical device of claim 10 wherein the working electrode is constituted of an electronically conductive oxide.

17. The improved electrochemical device of claim 16 wherein the oxide of the working electrode is ruthenium dioxide.

18. The improved electrochemical device of claim 10 wherein the reference electrode comprises a metal selected from the group consisting of tin, lead, bismuth and silver.

19. In an electrochemical device for measuring the partial pressure of oxygen in a liquid or gaseous atmosphere having a reference electrode, a working electrode responsive to oxygen and a solid electrolyte, the improvement which comprises said electrolyte comprising a fluoride mixed with lead and tin doped with barium peroxide, said peroxide supplying the reactive ions for the working electrode and said reference electrode for maintaining constant, at least in its immediate vicinity, the chemical potential of the fluoride of the electrolyte, and which electrode comprises at least partially a mixture of a metal and the fluoride corresponding to that of the electrolyte.

* * * * *